(12) United States Patent
Simonet et al.

(10) Patent No.: US 9,766,212 B2
(45) Date of Patent: Sep. 19, 2017

(54) ULTRASONIC PROBE FOR CONTACT MEASUREMENT OF AN OBJECT AND ITS MANUFACTURING PROCESS

(71) Applicant: EUROPEAN AERONAUTIC DEFENCE AND SPACE COMPANY EADS FRANCE, Paris (FR)

(72) Inventors: Didier Simonet, Leguevin (FR); Nicolas Colin, Toulouse (FR)

(73) Assignee: AIRBUS GROUP SAS, Blagnac (FR)

( * ) Notice: Subject to any disclaimer, the term of this patent is extended or adjusted under 35 U.S.C. 154(b) by 249 days.

(21) Appl. No.: 14/433,642

(22) PCT Filed: Oct. 18, 2013

(86) PCT No.: PCT/EP2013/071829
§ 371 (c)(1),
(2) Date: Apr. 4, 2015

(87) PCT Pub. No.: WO2014/060574
PCT Pub. Date: Apr. 24, 2014

(65) Prior Publication Data
US 2015/0268198 A1 Sep. 24, 2015

(30) Foreign Application Priority Data

Oct. 19, 2012 (FR) ...................................... 1259985

(51) Int. Cl.
*C23C 14/34* (2006.01)
*G01H 11/08* (2006.01)
*G01N 29/28* (2006.01)

(52) U.S. Cl.
CPC ............. *G01N 29/28* (2013.01); *C23C 14/34* (2013.01); *G01H 11/08* (2013.01); *G01N 2291/2638* (2013.01)

(58) Field of Classification Search
CPC ........ G01H 11/08; C23C 14/34; G01N 29/28; G01N 2291/2638
USPC ............................................ 73/625; 29/25.35
See application file for complete search history.

(56) References Cited

U.S. PATENT DOCUMENTS

| | | | |
|---|---|---|---|
| 5,042,493 A * | 8/1991 | Saito ..................... | B06B 1/0622 29/25.35 |
| 5,744,898 A | 4/1998 | Smith et al. | |
| 8,206,792 B2 * | 6/2012 | Gollob ..................... | C23C 4/04 427/450 |
| 2002/0062079 A1* | 5/2002 | Tahara ..................... | A61B 8/00 600/459 |

(Continued)

OTHER PUBLICATIONS

Denslow et al., "Waterless coupling of ultrasound from planar contact transducers to curved and irregular surfaces during non-destructive ultrasonic evaluations," Proc. of SPIE, Mar. 23, 2012, pp. 834711-1 to 834711-11, vol. 8347.

*Primary Examiner* — J M Saint Surin
(74) *Attorney, Agent, or Firm* — IM IP Law; C. Andrew Im

(57) ABSTRACT

An ultrasonic probe for contact measurement of an object and its manufacturing process. The ultrasonic probe has ultrasonic sensors securely fastened to a first face of a substrate. The opposite face of the substrate defines a measurement surface having a shape that is the imprint of the surface of the object to be measured to closely follow the latter when the surface of the object is brought into contact with the measurement surface.

9 Claims, 1 Drawing Sheet

(56) References Cited

U.S. PATENT DOCUMENTS

2002/0145134 A1* 10/2002 Olding .................. C03C 17/007
                                                          252/500
2011/0072905 A1    3/2011 Lam et al.

* cited by examiner

ULTRASONIC PROBE FOR CONTACT MEASUREMENT OF AN OBJECT AND ITS MANUFACTURING PROCESS

RELATED APPLICATIONS

This application is a §371 application from PCT/EP2013/071829 filed Oct. 18, 2013, which claims priority from French Patent Application No. 12 59985 filed Oct. 19, 2012, each of which is herein incorporated by reference in its entirety.

BACKGROUND OF THE INVENTION

Field of the Invention

The present invention relates to an ultrasonic probe for measuring, with contact, an object, and its manufacturing process. This ultrasonic measuring probe is particularly suitable for nondestructive testing of objects of complex geometry, such as certain mechanical parts for example.

The present invention is especially applicable to nondestructive testing in the aeronautical, space, automotive and rail-transportation fields, etc.

Technological Background

It is known to test structures, especially structures made of composites, with a view to detecting, nondestructively, possible surface and/or bulk defects in these structures.

Thus, ultrasonic measuring systems are known, these systems having the advantage of permitting testing of structures directly at manufacturing sites.

However, it is necessary to move the ultrasonic measuring system manually (typically done by a qualified person) or automatically. Guiding and locating means are then used in order to identify the part of the structure being measured.

Furthermore, in the case of structures having a complex geometry, it is necessary to carry out a number of scans possibly with different ultrasonic measuring frequencies.

These operations are time-consuming, tedious for the operators and expensive.

Moreover, certain structures, especially in the aeronautical field, must be tested in their entirety, which is not always possible with a through-transmission ultrasonic test method. Specifically, certain zones of the structure may not be accessible by this type of testing technique.

The present invention aims to overcome these various drawbacks by providing an ultrasonic measuring system for nondestructive testing of objects such as mechanical or structural parts, which measuring system has a simple design and operating mode and permits at least one portion of an object of complex geometry to be measured in a single scan.

Another subject of the present invention is a particularly simple and flexible process for manufacturing such an ultrasonic measuring system.

OBJECT AND SUMMARY OF THE INVENTION

For this purpose, the invention relates to an ultrasonic probe for measuring, with contact, an object, said object having an irregular surface.

According to the invention, this ultrasonic probe comprises ultrasonic sensors securely fastened to a first face of a substrate, the opposite face of this substrate defining a measurement surface, this measurement surface having a shape that is the imprint of the surface of the object to be measured so as to closely follow the latter surface when the surface of the object is brought into contact with said measurement surface.

This ultrasonic probe thus contributes to the field of pulse-echo ultrasonic testing in which one and the same sensor is used both to emit the ultrasonic waves and receive the ultrasonic waves reflected by the object to be analyzed, this sensor being position coded.

The expression "irregular surface of the object" is understood to mean that this surface of the object contains at least one corner. This surface of the object may thus have an L, V or even U shape. By way of counter example, this surface of the object to be measured is not a strictly flat surface or the outside surface of a cylinder, the latter being regular.

Advantageously, the measurement surface of this ultrasonic probe covers at least half the total surface of the object to be measured, thereby making it possible to measure, in a single scan, the portion of the object outside surface of which is brought into contact with the measurement surface of the probe.

Of course, the measurement surface has a shape that is the imprint of the surface of the object to be measured only to within manufacturing tolerances, it being understood that said surface will be defined relative to the theoretical sides that the object to be measured should have.

Advantageously, the substrate has a uniform thickness.

In various embodiments of this ultrasonic probe, the present invention also relates to the following features, which must be considered in isolation or in any of their technically possible combinations:

this probe comprises a coupling element intended to ensure matching of the acoustic impedance between said object and said probe, said coupling element comprising an envelope such as a membrane defining an interior volume in which a liquid coupling medium is placed.

Preferably, this liquid coupling medium is water or a coupling gel.

Purely by way of illustration, this ultrasound coupling gel is an aqueous gel comprising polyols such as that sold by METALSCAN, rue Désiré Gilot, 71100 Saint-Rémy under the name Couplant UT 5.

Advantageously, this envelope has an acoustic impedance substantially equal to that of water, the latter being $1.5 \times 10^6$ Pa·s/m. By way of nonlimiting example, this envelope has an acoustic impedance that is equal to within 15% to that of water.

Preferably, said coupling element has a thickness smaller than or equal to 3 mm.

Apart from matching of the acoustic impedance between the object to be measured and the ultrasonic probe, said coupling element also ensures adjustment or compliance of the surface of the object to be measured with the measurement surface of the ultrasonic probe, thereby compensating for possible divergences especially related to the manufacturing tolerances of the object.

said ultrasonic sensors form an array of piezoelectric ceramic sensors securely fastened to this substrate.

Preferably, said substrate is a metal substrate or a substrate made of polyimide or of a graphite/epoxy composite.

Purely by way of illustration, the metal substrate is made of aluminum, steel, stainless steel, titanium, nickel or copper, inter alia.

this probe comprises an electronic means for processing the electrical signals delivered by the ultrasonic sensors when they receive ultrasound.

The invention also relates to a process for manufacturing an ultrasonic probe for ultrasonic testing of an object with contact, in which at least the following steps are carried out:

a) providing a carrier having an internal surface defining a measurement surface of said probe and a smooth external surface, said carrier having been shaped so that this internal surface is an imprint of the surface of the object to be measured so as to closely follow the latter surface when the object is brought into contact with this internal surface;

b) mixing a ceramic powder in a sol-gel solution so as to form a uniform dispersion;

c) depositing a coating containing said uniform dispersion on the external surface of said carrier using a thin-film deposition method;

d) baking said coating thus formed at a temperature T higher than or equal to 100° C. for a time T in order to form a piezoelectric ceramic coating on said external surface;

e) optionally repeating steps b), c) and d) in order to form a piezoelectric ceramic block comprising at least two ceramic coatings; and f) forming at least one electrode on the external surface of said coating or said piezoelectric ceramic block in order to define a sensor.

Advantageously, in step c), said coating containing said dispersion is deposited uniformly in order to obtain an even ceramic coating thickness over said carrier.

In addition, the first coating containing said dispersion being deposited on the non-rough external surface of the carrier, the baking temperature of at least 100° C. implemented in step d) to bake each ceramic coating ensures that the final thickness of the coating or ceramic block is uniform.

Before step f), said coating or said piezoelectric ceramic block thus formed is polarized. This polarization may be obtained by a corona discharge process.

By way of example, in step f), the electrodes may be formed by a silver metallization paste.

In various embodiments of this manufacturing process, the present invention also relates to the following features, which must be considered in isolation or in any of their technically possible combinations:

a coupling element intended to ensure matching of the acoustic impedance between said object and said probe is placed on said measurement surface defined by the internal surface of the substrate, said coupling element comprising an envelope defining an interior volume in which a liquid coupling medium is placed.

Preferably, this liquid coupling medium is water or a coupling gel.

in step f), a plurality of electrodes are produced on the surface of said coating or said piezoelectric ceramic block so as to form an array of piezoelectric sensors.

Preferably, these sensors are spaced equidistantly.

said ceramic powder is maintained in a range of 30% to 50% by weight of said solution.

This ceramic powder is advantageously selected from the group comprising BIT (bismuth titanium composite), silica, alumina, silicon carbide, etc.

The PZT ceramic powder sold under the name Pz23 by FERROPERM PIEZOCERAMICS, DK-3490 Kvistgård, is particularly suitable for the present invention.

said thin-film deposition method is a sputtering deposition method.

after step f), each of said sensors is connected to an electronic means for processing the signals delivered by these sensors when they receive ultrasound.

before step f), the thickness of said at least one ceramic coating is controlled so that the ceramic block thus obtained corresponds to the measurement frequencies of said probe.

said object having an irregular surface, the internal surface of said carrier is shaped so that this internal surface is an imprint of the irregular surface of the object to be measured.

The present invention also relates to an apparatus for nondestructive testing of parts by ultrasound.

According to the invention, this apparatus comprises two ultrasonic measuring probes such as described above, said probes being intended to closely follow at least one opposite face of this part, at least one of these probes being movable so that these probes can be moved from each other, in order to position or remove the part to be measured, and toward each other, with a view to covering entirely the surface of this part in order to nondestructively test it in a single scan, or even in a single pass.

By way of example, this apparatus therefore comprises a means for conveying the part to be measured and/or gripping this part in order to place it on the measurement surface of one of said ultrasonic measuring probes, and a means for moving the other ultrasonic measuring probe relative to the ultrasonic measuring probe receiving the part to be measured.

This nondestructive testing process may be integrated into a part manufacturing line, thus ensuring simple and rapid in-line testing of these parts.

BRIEF DESCRIPTION OF THE DRAWINGS

Other particular advantages, aims and features of the present invention will become apparent from the following completely non-limiting description given, by way of example, with regard to the appended figures, in which.

DETAILED DESCRIPTION OF AN EMBODIMENT OF THE INVENTION

Firstly, it will be noted that the figures are not to scale.

Figure 1:
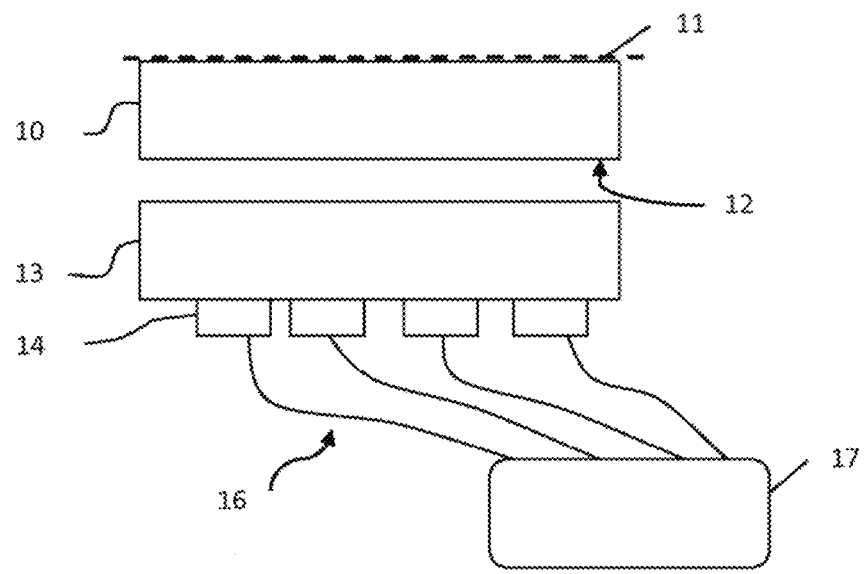
FIG. 1 schematically shows an exploded view of a contact ultrasonic measuring probe according to one particular embodiment of the present invention.

FIG. 1 schematically shows an exploded view, for the sake of clarity, of the various constituent elements of a contact ultrasonic measuring probe according to one particular embodiment of the present invention.

This measuring probe comprises a substrate 10, here made of a metal such as aluminum, this substrate 10 having been shaped so that its internal surface 11 is the imprint, to within manufacturing tolerances, of the outside surface of a portion of a mechanical part to be measured.

Thus, when this portion of the mechanical part of complex geometry is placed making direct contact with the internal surface 11 of the substrate 10 thus shaped, its outside surface closely follows the internal surface 11 of the substrate 10 to within manufacturing tolerances. By way of illustration, the substrate 10 may be shaped by deep drawing.

The piezoelectric ceramic block 13 comprising a plurality of piezoelectric ceramic layers is joined to the external surface 12 of this substrate 10, said layers having been formed in succession.

Each of these various layers is obtained by a method for depositing by sputtering a PZT sol-gel solution in which a piezoelectric (PZT) ceramic powder has been uniformly dispersed, the size of the particles of the powder typically being comprised between 1 and 80 μm, the coating thus uniformly deposited being baked at a temperature of at least 100° C. by means of a source of hot air such as a heat gun.

Advantageously, the PZT sol-gel solution acts as an agent binding the ceramic powder to the corresponding surface on which the coating is deposited.

The thickness of each ceramic coating of the block 13 is typically comprised between 1 μm and 20 μm, the total thickness of this piezoelectric ceramic block, which is equal or substantially equal over the entirety of this block, being defined so that the ultrasonic probe functions at a central frequency typically comprised between 1 and 30 MHz (high frequency) or typically comprised between 20 and 50 kHz (low frequency).

On the external surface of this piezoelectric ceramic block 13 is placed a set of electrodes 14, these electrodes 14 optionally being regularly spaced. The thickness of the ceramic block 13, between an electrode 14 and the substrate 10, defines an ultrasonic sensor.

Each sensor of this ultrasonic probe is connected by a cable 16 to a multichannel electronic means 17 that supplies power. A central processor (not shown) connected to the multichannel electronic means 17 processes the results measured by said ultrasonic sensors of the ultrasonic probe.

Figure 2:
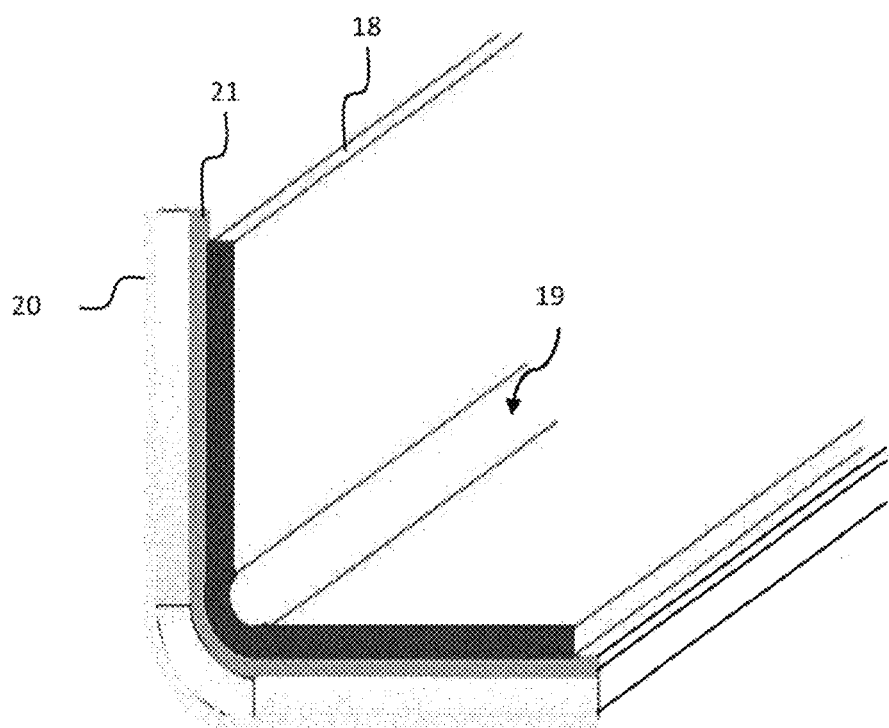
FIG. 2 shows one method of implementing the present invention in nondestructive testing of a structural part of an aircraft.

FIG. 2 shows one method of implementing the present invention in nondestructive testing of a structural part 18 of an aircraft.

This structural part 18 is curved so that it has a rounded portion 19 placed between two flat flanges. The contact ultrasonic measuring system 20 employed to test the quality of this structural part 18 has a measurement surface that is the imprint of the outside surface of this structural part 18 so as to closely follow the latter surface when this outside surface of the part is brought into contact with this measurement surface.

A coupling element 21 consisting of an envelope such as a membrane, bounding an interior volume in which water is placed, is interposed between this outside surface and the measurement surface of the system 20. This coupling element 21 is intended to ensure matching of the acoustic impedance between the part and the measuring system 20.

The invention claimed is:

1. A process for manufacturing an ultrasonic probe for ultrasonic testing of an object with contact, comprising the steps of:
   providing a carrier having an internal surface defining a measurement surface of said ultrasonic probe and a smooth external surface, said carrier being shaped so that the internal surface is an imprint of a surface of the object to be measured to closely follow the surface of the object in contact with the internal surface;
   mixing a ceramic powder in a sol-gel solution to form a uniform dispersion;
   depositing a coating containing said uniform dispersion on the external surface of said carrier using a thin-film deposition method;
   baking said coating at a temperature higher than or equal to 100° C. for a predetermined time to form a piezoelectric ceramic coating on said external surface;
   optionally repeating the steps of mixing, depositing and baking to form a piezoelectric ceramic block comprising at least two ceramic coatings; and
   forming at least one electrode on an external surface of said coating or said piezoelectric ceramic block to define a sensor.

2. The process as claimed in claim 1, further comprising the step of placing a coupling element configured to ensure matching of an acoustic impedance between said object and said ultrasonic probe on said measurement surface, said coupling element comprising an envelope defining an interior volume in which a liquid coupling medium is placed.

3. The process as claimed in claim 2, wherein said liquid coupling medium is water or a coupling gel.

4. The process as claimed in a claim 1, further comprising the step of producing a plurality of electrodes on the external surface of said coating or said piezoelectric ceramic block to form an array of piezoelectric sensors.

5. The process as claimed in claim 4, further comprising the step of connecting each of said piezoelectric sensors to an electronic device that processes signals received from the piezoelectric sensors in response to reception of ultrasound.

6. The process as claimed in claim 1, further comprising the step of maintaining said ceramic powder in a range of 30% to 50% by weight of said sol-gel solution.

7. The process as claimed in claim 1, wherein said thin-film deposition method is a sputtering deposition method.

8. The process as claimed in claim 1, further comprising step of controlling thickness of said at least one ceramic coating so that the piezoelectric ceramic block corresponds to measurement frequencies of said ultrasonic probe.

9. The process as claimed in claim 1, wherein said object has an irregular surface; and wherein the internal surface of said carrier is shaped so that the internal surface is an imprint of the irregular surface of the object to be measured.

* * * * *